United States Patent
Lee et al.

(10) Patent No.: US 11,229,810 B2
(45) Date of Patent: Jan. 25, 2022

(54) METHODS AND SYSTEMS FOR PRODUCING NEURONAL LESIONS USING MAGNETIC RESONANCE AND ACOUSTIC ENERGY

(71) Applicants: University of Virginia Patent Foundation, Charlottesville, VA (US); The Board of Trustees of the Leland Stanford Junior University, Palo Alto, CA (US)

(72) Inventors: Kevin S. Lee, Charlottesville, VA (US); Edward H. Bertram, Charlottesville, VA (US); Max Wintermark, Menlo Park, CA (US)

(73) Assignees: University of Virginia Patent Foundation, Charlottesville, VA (US); The Board of Trustees of the Leland Stanford Junior University, Stanford, CA (US)

( * ) Notice: Subject to any disclaimer, the term of this patent is extended or adjusted under 35 U.S.C. 154(b) by 602 days.

(21) Appl. No.: 15/981,186

(22) Filed: May 16, 2018

(65) Prior Publication Data
US 2018/0333593 A1   Nov. 22, 2018

Related U.S. Application Data

(60) Provisional application No. 62/507,272, filed on May 17, 2017.

(51) Int. Cl.
*A61N 7/00* (2006.01)
*G01R 33/50* (2006.01)
(Continued)

(52) U.S. Cl.
CPC .............. *A61N 7/00* (2013.01); *A61B 5/0036* (2018.08); *A61B 5/055* (2013.01); *A61B 5/7485* (2013.01);
(Continued)

(58) Field of Classification Search
CPC .............. A61N 7/00; A61N 2007/0095; A61N 2007/0039; A61N 2007/003;
(Continued)

(56) References Cited

U.S. PATENT DOCUMENTS 6,207,709 B1 *  3/2001  Varasi ................... C07C 233/47
                                                    514/538
6,430,430 B1 *  8/2002  Gosche ................. G06T 7/0012
                                                    600/410
(Continued)

OTHER PUBLICATIONS

Kinoshita ["Targeted delivery of antibodies through the blood-brain barrier by MRI-guided focused ultrasound" Biochemical and Biophysical Research Communications 340 (2006) 1085-1090] (Year: 2006).*

(Continued)

*Primary Examiner* — Oommen Jacob
(74) *Attorney, Agent, or Firm* — Schwegman Lundberg & Woessner, P.A.

(57) ABSTRACT

Methods and systems are described for producing non-invasive and targeted neuronal lesions using magnetic resonance and acoustic energy. Imaging data corresponding to a region of interest is obtained, the region of interest within an imaging subject. Information indicative of a target region within the region of interest is received from the obtained imaging data. Focused acoustic energy directed to the target region within the region of interest is generated to disrupt a barrier between a therapeutic agent and parenchymal tissue in response to insonification by the focused acoustic energy, (Continued)

the therapeutic agent comprising a neurotoxin and microbubbles.

21 Claims, 4 Drawing Sheets

(51) Int. Cl.
| | | |
|---|---|---|
| *G01R 33/48* | (2006.01) | |
| *A61B 5/055* | (2006.01) | |
| *A61M 37/00* | (2006.01) | |
| *A61B 5/00* | (2006.01) | |
| *G01R 33/56* | (2006.01) | |
| *A61B 90/00* | (2016.01) | |
| *A61B 34/00* | (2016.01) | |

(52) U.S. Cl.
CPC ..... *A61M 37/0092* (2013.01); *G01R 33/4808* (2013.01); *G01R 33/4814* (2013.01); *G01R 33/50* (2013.01); *A61B 5/0042* (2013.01); *A61B 5/4839* (2013.01); *A61B 34/25* (2016.02); *A61B 2090/374* (2016.02); *A61B 2576/026* (2013.01); *A61M 2205/05* (2013.01); *A61M 2205/058* (2013.01); *A61M 2210/0693* (2013.01); *A61N 2007/003* (2013.01); *A61N 2007/0039* (2013.01); *A61N 2007/0095* (2013.01); *G01R 33/5601* (2013.01)

(58) Field of Classification Search
CPC ..... A61B 5/0036; A61B 5/7485; A61B 5/055; A61B 5/0042; A61B 2090/374; A61B 2576/026; A61B 5/4839; A61B 34/25; G01R 33/4808; G01R 33/4814; G01R 33/50; G01R 33/5601; A61M 37/0092; A61M 2205/058; A61M 2205/05; A61M 2210/0693
See application file for complete search history.

(56) References Cited

U.S. PATENT DOCUMENTS

| | | | | |
|---|---|---|---|---|
| 7,896,821 | B1* | 3/2011 | Magnin | A61H 23/0245 |
| | | | | 601/2 |
| 9,096,848 | B2* | 8/2015 | Kimmel | C12M 35/04 |
| 9,119,951 | B2* | 9/2015 | Gertner | A61B 90/37 |
| 10,517,564 | B2* | 12/2019 | Konofagou | A61B 8/5223 |
| 2003/0216648 | A1* | 11/2003 | Lizzi | A61B 17/2256 |
| | | | | 600/439 |
| 2004/0049134 | A1* | 3/2004 | Tosaya | A61H 23/0236 |
| | | | | 601/2 |
| 2004/0092809 | A1* | 5/2004 | DeCharms | A61B 5/4088 |
| | | | | 600/410 |
| 2004/0186372 | A1* | 9/2004 | Boernert | G01R 33/5676 |
| | | | | 600/410 |
| 2004/0210135 | A1* | 10/2004 | Hynynen | A61B 8/54 |
| | | | | 600/439 |
| 2005/0249667 | A1* | 11/2005 | Tuszynski | A61B 8/08 |
| | | | | 424/9.3 |
| 2006/0015162 | A1* | 1/2006 | Edward | A61B 18/1477 |
| | | | | 607/105 |
| 2007/0059247 | A1* | 3/2007 | Lindner | A61K 49/223 |
| | | | | 424/9.52 |
| 2007/0133852 | A1* | 6/2007 | Collins | G01R 33/5601 |
| | | | | 382/128 |
| 2007/0267011 | A1* | 11/2007 | Deem | A61K 9/0043 |
| | | | | 128/200.23 |
| 2009/0290765 | A1* | 11/2009 | Ishii | A61B 6/037 |
| | | | | 382/128 |
| 2010/0080432 | A1* | 4/2010 | Lilja | G06T 7/0012 |
| | | | | 382/131 |
| 2010/0143241 | A1* | 6/2010 | Johnson | A61K 49/223 |
| | | | | 424/1.11 |
| 2010/0179415 | A1* | 7/2010 | Wenzel | G06T 7/0012 |
| | | | | 600/411 |
| 2011/0184337 | A1* | 7/2011 | Evans | A61P 9/12 |
| | | | | 604/22 |
| 2011/0208095 | A1* | 8/2011 | Jolesz | A61N 7/00 |
| | | | | 601/2 |
| 2011/0319765 | A1* | 12/2011 | Gertner | A61N 7/02 |
| | | | | 600/453 |
| 2012/0109018 | A1* | 5/2012 | Gertner | A61N 7/02 |
| | | | | 601/2 |
| 2012/0172708 | A1* | 7/2012 | Anand | A61N 7/02 |
| | | | | 600/411 |
| 2018/0333593 | A1* | 11/2018 | Lee | A61B 5/0036 |

OTHER PUBLICATIONS

Zhang ["Non-Invasive, Focal Disconnection of Brain Circuitry using Magnetic Resonance-Guided Low-Intensity Focused Ultrasound to Delivers Neurotoxin" Ultrasound in Medicine and Biology vol. 42, No. 9, 2016]. (Year: 2016).*

Zhang, Y., et al., "Non-invasive, focal disconnection of brain circuitry using magnetic resonance-guided low-intensity focused ultrasound to deliver a neurotoxin", Ultrasound Med Biol. Sep. 2016;42(9):2261-9. doi: 10.1016/j.ultrasmedbio.2016.04.019. Epub May 31, 2016, (2016), 2261-2269.

* cited by examiner

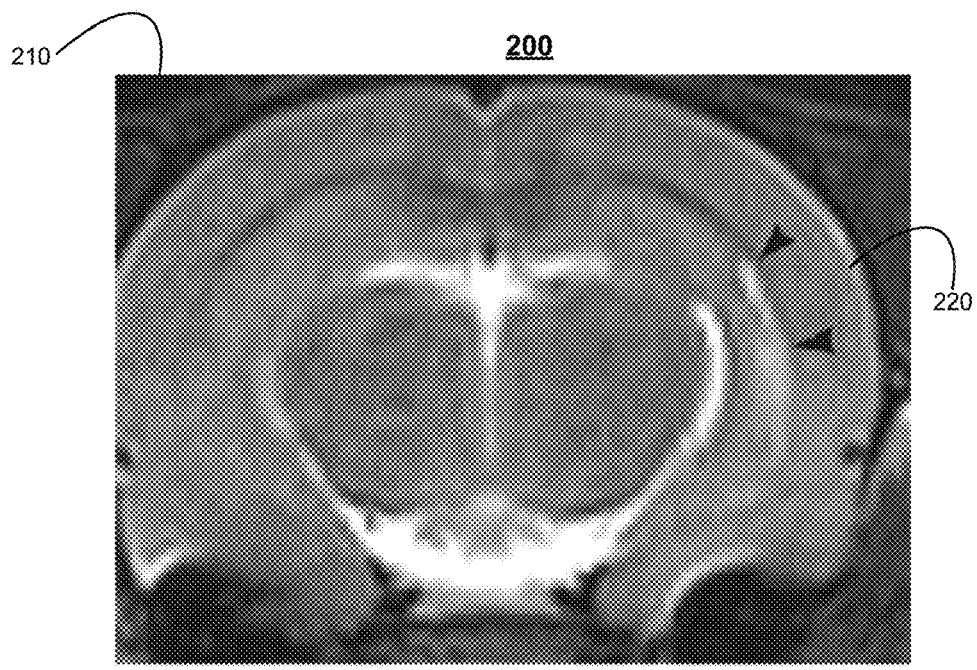
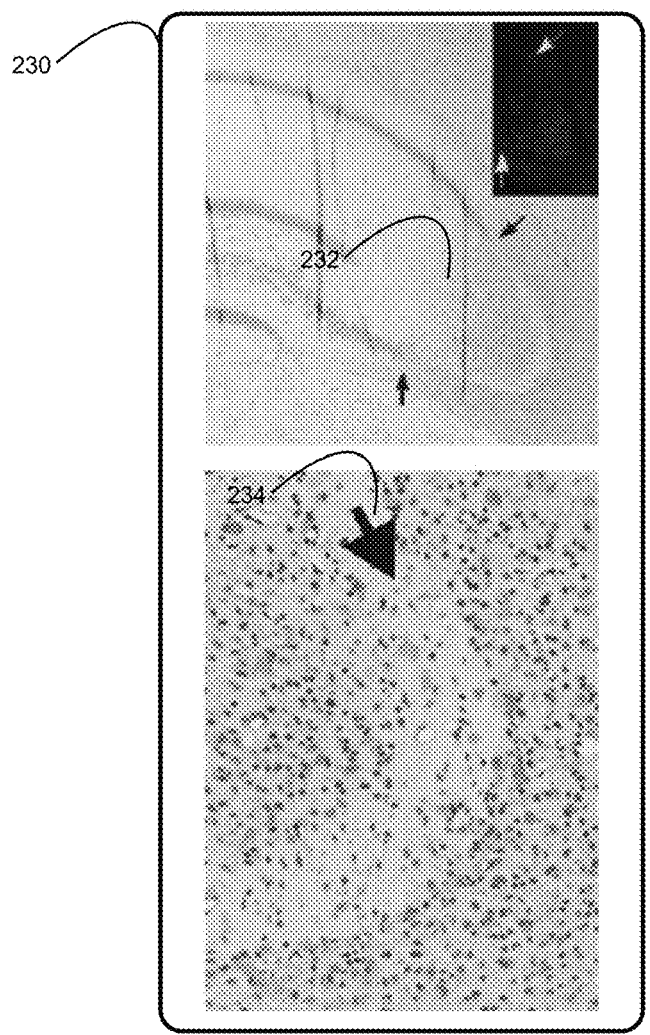
FIG. 2

300

310
OBTAIN IMAGING DATA CORRESPONDING TO A REGION OF INTEREST, THE REGION OF INTEREST WITHIN AN IMAGING SUBJECT

320
RECEIVE INFORMATION INDICATIVE OF A TARGET REGION WITHIN THE REGION OF INTEREST FROM THE OBTAINED IMAGING DATA

330
GENERATE FOCUSED ACOUSTIC ENERGY DIRECTED TO THE TARGET REGION WITHIN THE REGION OF INTEREST TO DISRUPT A BARRIER BETWEEN A THERAPEUTIC AGENT AND PARENCHYMAL TISSUE IN RESPONSE TO INSONIFICATION BY THE FOCUSED ACOUSTIC ENERGY, THE THERAPEUTIC AGENT COMPRISING A NEUROTOXIN AND MICROBUBBLES

FIG. 3

METHODS AND SYSTEMS FOR PRODUCING NEURONAL LESIONS USING MAGNETIC RESONANCE AND ACOUSTIC ENERGY

CLAIM OF PRIORITY

This patent application claims the benefit of priority of Lee, et al., U.S. Provisional Patent Application Ser. No. 62/507,272, titled "Non-invasive Method and System for Localized Lesion Production Using Magnetic Resonance-guided Ultrasound and Cellular Toxins," filed on May 17, 2017, the entirety of which is hereby incorporated by reference herein.

FIELD OF THE DISCLOSURE

This document pertains generally, but not by way of limitation, to focused ultrasound surgery (FUS), and more particularly to apparatus and techniques for producing neuronal lesions using magnetic resonance (MR) imaging and FUS.

BACKGROUND

Neurological diseases ranging from epilepsy to movement disorders may evade effective medical management for many patients. When conventional pharmacotherapeutic approaches have been exhausted for such disorders, surgery becomes a potential modality of choice. For example, patients with temporal lobe epilepsy, that is refractory to various combinations of anti-epileptic drugs, become candidates for surgical resection of part or all of the temporal lobe. This type of surgery can be highly invasive and require the removal of substantial amounts of cortical tissue. Complications can include bleeding, infection, blood clots, stroke, seizures, swelling of the brain, and nerve damage. Moreover, persistent functional deficits in memory, language comprehension, and visual processing may occur. Alternatives to major invasive procedures include minimally-invasive laser ablation and non-invasive radiosurgery. While these approaches are less risky, may produce reasonable seizure management, and may reduce the incidence of functional deficits, such approaches may still present substantial potential side effects.

Overview

The present inventors have developed a technique to use Magnetic Resonance (MR) imaging combined with focused acoustic energy (e.g., Focused Ultrasound) to surgically produce neuronal lesions in a subject (e.g., a living organism or human being). Such a technique can be referred to as "minimally invasive" at least in contrast to more invasive surgical resection approaches. Techniques as described herein can be used, for example, to disconnect critical pathways contributing to neurological disease. The subject may be referred to below as the patient. These neuronal lesions may be produced in any part of a patient's body but for illustrative purposes will be discussed in connection with brain tissue. One way to produce such lesions may include introducing a therapeutic agent (e.g., a neurotoxin) to damage tissue in a target region (e.g., of the brain). However, the target region may include a barrier that prevents such a therapeutic agent (e.g., the neurotoxin) from entering the target region. For example, the target region may include the brain and such neurotoxins may have substantially low blood-brain-barrier (BBB) permeability and, as such, such neurotoxins will be inhibited or prevented from inducing neuronal degeneration in the absence of other agents or techniques, as described herein.

The present inventors have developed, among other things, a technique to enable such therapeutic agents to enter the region of interest despite the barrier in the region of interest that otherwise prevents such therapeutic agents from entering the region. Particularly, the present inventors have developed a technique to enable a neurotoxin to enter a target region of the brain despite the substantially low BBB permeability of the neurotoxin. The inventors have recognized that application of focused acoustic energy (e.g., low intensity ultrasound) to a target region of interest in a subject (e.g., a brain) can disrupt a barrier between a therapeutic agent and parenchymal tissue in the region of interest (e.g., the BBB). Accordingly, by generating focused acoustic energy (e.g., guided by an MR image) directed to the target region, a barrier between a therapeutic agent and parenchymal tissue is disrupted, allowing the therapeutic agent, including a neurotoxin, to enter and permeate the target region to create a lesion in a desired location.

In addition, the present inventors have recognized that in the presence of microbubbles, lower intensity focused acoustic energy can be used to disrupt the barrier, as compared to an acoustic energy level used in the absence of such microbubbles. In particular, introducing microbubbles into the blood circulation can reduce the intensity of energy needed by the focused ultrasound to disrupt the BBB significantly. In this manner, a neurotoxin can be delivered to a specific and restricted area of the brain in order to destroy target neurons and disrupt central nervous system (CNS) circuitry with minimal or no damage to any other region of the brain or the patient's body.

An embodiment can include, or can optionally be combined with the subject matter of one or any combination of other embodiments herein to include, subject matter (such as an apparatus, a method, a means for performing acts, or a machine readable medium including transitory or non-transitory instructions that, when performed by the machine, can cause the machine to perform acts), such as obtaining imaging data corresponding to a region of interest, the region of interest within an imaging subject; receiving information indicative of a target region within the region of interest, from the obtained imaging data; and generating focused acoustic energy directed to the target region within the region of interest to disrupt a barrier between a therapeutic agent and parenchymal tissue in response to insonification by the focused acoustic energy, the therapeutic agent including a neurotoxin and microbubbles.

In an example, the imaging data corresponding to a region of interest, the region of interest within an imaging subject, can be obtained using a magnetic resonance. For example, a magnetic resonance device may generate magnetic resonance and capture an image of the region of interest under the influence of the magnetic resonance. In some implementations, the image may be captured in accordance with at least one of a T1-weighted spin echo imaging protocol, a T2-weighted gradient recalled echo imaging protocol, and a T2-weighted turbo spin-echo imaging protocol.

In some implementations, the captured image may be enhanced using a contrast agent. For example, a contrast agent may be administered to a subject and subsequently, magnetic energy may be applied to a region of interest in the subject to detect a reaction of the contrast agent in the region of interest to the magnetic energy. The reaction intensity may be mapped in different order of magnitude using different color schemes in the image to represent the reaction in the region of interest. In some implementations, the contrast agent may include gadodiamide contrast, but other contrast agents may be used.

In an example, a therapeutic agent may be administered to the subject. In particular, a processing circuit may generate an instruction to administer the therapeutic agent that includes the microbubbles and neurotoxin. The instruction may be presented on a display to instruct a technician or doctor to inject intravenously or orally the therapeutic agent. In some implementations, the processing circuit may automatically administer the therapeutic agent. In such circumstances, the processing circuit may transmit the instruction to an injection system (or administration system) that is connected to the subject. The instruction may indicate, to the injection system, an amount and time for injecting the therapeutic agent. In some implementations, the injection system may include multiple types of contrasts, therapeutic agents and other chemicals. In such circumstances, the instruction may inform the injection system of which one of the chemicals and/or therapeutic agents to select for injection or administration to the subject.

In an example, the region of interest comprises a brain of the imaging subject, the barrier comprises blood-brain-barrier (BBB), the neurotoxin may include a chemical with substantially low BBB permeability. In particular, the brain of the imaging subject may have a region afflicted by a neurological disease. The target region may include the region of the brain with the neurological disease that is sought to be therapeutically disconnected. While the target region is being insonified, the BBB in the target region is disrupted, thereby allowing the neurotoxin to enter the target region and destroy primary neurons in the target region in a targeted manner. In some implementations, the neurotoxin may include quinolinic acid.

In an example, the target region of interest may be indicated or identified automatically. For example, imaging data of a plurality of sections within the region of interest may be compared to a model representing neurological disease. A level of similarity between a first of the plurality of sections and the model may be determined to exceed a threshold. In response to determining that the level of similarity exceeds the threshold, the target region in the first of the plurality of sections may be selected, identified, or indicated as the target region. In another example, user input may be received that selects the target region from a plurality of regions in the region of interest.

In some embodiments, a system that includes a magnetic resonance imaging system, a memory circuit, a processor circuit and an acoustic energy generator may be provided. The magnetic resonance imaging system may be configured to obtain imaging data corresponding to a region of interest, the region of interest within an imaging subject. The memory circuit may be configured to store the obtained imaging data. The processor circuit may be coupled to the memory circuit and may be configured to receive information indicative of a target region within the region of interest from the stored imaging data. The acoustic energy generator coupled to an acoustic transducer may be configured to generate focused acoustic energy directed to the target region within the region of interest to disrupt a barrier between a therapeutic agent and parenchymal tissue in response to insonification by the focused acoustic energy, the therapeutic agent comprising a neurotoxin and microbubbles.

In an example, the focused acoustic energy may include low intensity ultrasound.

In an example, the magnetic resonance imaging system may be further configured to generate magnetic resonance and capture an image of the region of interest under the influence of the magnetic resonance, wherein the image is captured in accordance with at least one of T1-weighted spin echo imaging, T2-weighted gradient recalled echo imaging, and T2-weighted turbo spin-echo imaging. In some implementations, the captured image may be enhanced using a contrast agent. In some implementations, the contrast agent may include gadodiamide contrast, but any other type of contrast agent may be used.

In an example, the processor circuit may be further configured to generate an instruction to administer the therapeutic agent. The instruction may be presented on a display to instruct a technician or doctor to inject the therapeutic agent intravenously or orally. In some implementations, the processing circuit may automatically administer the therapeutic agent. In such circumstances, the processing circuit may transmit the instruction to an injection system that is connected to the subject. The instruction may indicate to the injection system an amount and time for injecting the therapeutic agent. In some implementations, the injection system may include multiple types of contrasts, therapeutic agents and other chemicals. In such circumstances, the instruction may inform the injection system of which one of the chemicals and/or therapeutic agents to select for injection or administration to the subject.

In an example, the region of interest comprises a brain of the imaging subject, the barrier comprises blood-brain-barrier (BBB), the neurotoxin may include a chemical with substantially low BBB permeability. In particular, the brain of the imaging subject may have a region that has a neurological disease. The target region may include the region of the brain with the neurological disease that is sought to be therapeutically disconnected. While the target region is being insonified by the system, the BBB in the target region is disrupted thereby allowing the neurotoxin to enter the target region and destroy primary neurons in the target region. In some implementations, the neurotoxin may include quinolinic acid.

In an example, the processor circuit may be configured to receive information indicative of the target region within the region of interest by comparing the imaging data of a plurality of sections within the region of interest to a model representing neurological disease. The processor circuit may be configured to determine that a level of similarity between a first of the plurality of sections and the model exceeds a threshold. The processor circuit may be configured to, in response to determining that the level of similarity exceeds the threshold, select as the target region the first of the plurality of sections. In some implementations, the processor circuit may be configured to receive information indicative of the target region within the region of interest by receiving user input that selects the target region from a plurality of regions in the region of interest.

This summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 2 illustrates exemplary images of a target area after being insonified in the presence of a therapeutic agent, in accordance with various examples.

FIG. 3 illustrates an exemplary flowchart of a process for using acoustic energy and a therapeutic agent, in accordance with various examples.

DETAILED DESCRIPTION

Figure 1:
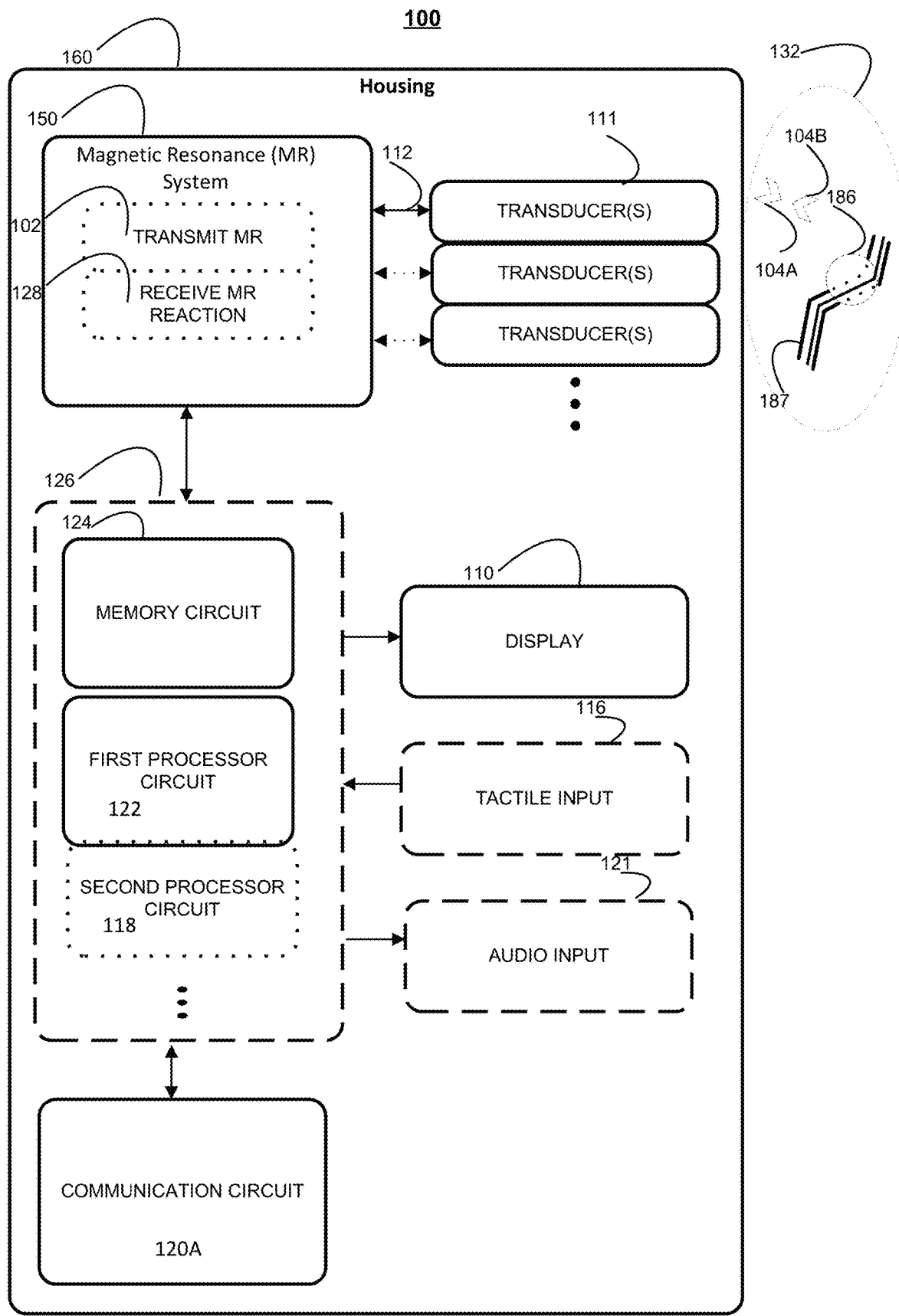
FIG. 1 illustrates generally an example of portions of a system that can include a magnetic resonance and acoustic energy generation system, and portions of an environment in which the system can be used.

FIG. 1 illustrates generally an example of portions of a system 100 that can include a magnetic resonance imaging and acoustic energy generation system, and portions of an environment in which the system 100 can be used. Such a system 100 can be used to perform one or more techniques described herein, such as obtaining imaging data corresponding to a region of interest, the region of interest within an imaging subject; receiving information indicative of a target region within the region of interest, from the obtained imaging data; and generating focused acoustic energy directed to the target region within the region of interest to disrupt a barrier between a therapeutic agent and parenchymal tissue in response to insonification by the focused acoustic energy, the therapeutic agent comprising a neurotoxin and microbubbles. For example, system 100 may be use a low intensity focused ultrasound (optionally combined with microbubbles) to transiently disrupt the BBB in order to deliver a neurotoxin (e.g., quinolinic acid (QA)).

In an example, the system 100 can include a first processor circuit 122, a memory circuit 124, a display 110, one or more transducers 111, an analog front-end (e.g., a magnetic resonance (MR) system 150) coupled to an array of transducers 111, such as via a bus 112, one or more analog-to-digital (A/D) converters, and digital logic. The magnetic resonance (MR) system 150 can include one or more of a transmit MR 102, a receive MR reaction 128, or other elements. In some embodiments, transmit MR 102 may include circuitry for transmitting magnetic resonance and receive MR reaction 128 may include magnetic resonance imaging circuitry configured to detect magnetic energy in an imaging subject to which transmit MR 102 provided magnetic resonance. In an illustrative example, the magnetic resonance system 150 can include an MRI system. Computer system 126 may instruct MR system 150 to capture one or more images using any number of different techniques. For example, computer system 126 may instruct magnetic resonance system 150 to capture one or more images (e.g., execute an imaging excitation sequence, obtain imaging information elicited by the excitation sequence, and construct one or more images) of an imaging subject in accordance with at least one of a T1-weighted spin echo imaging protocol, a T2-weighted gradient recalled echo imaging protocol, and a T2-weighted turbo spin-echo imaging protocol. Any other known imaging protocol or technique may be used instead of or in combination with the image captured in accordance with at least one of T1-weighted spin echo imaging protocol, T2-weighted gradient recalled echo imaging protocol, and T2-weighted turbo spin-echo imaging protocol.

One or more of the memory circuit 124, the first processor circuit 122, or one or more additional processor circuits such as a second processor circuit 118 can be included in a computer system 126. Such as computer system 126 can include a hand-held or tablet computer, a desktop computer, a laptop computer, a computer server, or a combination of one or more general purpose or special purpose computers, such as configured to obtain ultrasonic echo information from a transducer block, such as via a wired or wireless communication link and/or MR imaging information from an MR imaging circuitry. Memory circuit 124 may store the images captured by magnetic resonance system 150.

In an example, a region of interest 132 can include one or more actual targets such as a first target 186. The region of interest 132 can be excited (e.g., insonified, etc.) such as using energy provided by the transducer array 111, such as under the control of the first processor circuit 122. For example, a transmitted ultrasonic energy 104A can propagate through the region of interest 132, and a portion of the transmitted energy 104A can be scattered or reflected by one or more targets, such as the first target 186, to provide an echo 104B. The transducer array 111 can be configured to receive a portion of the echo 104B. An analog front end circuit can be configured for processing the resulting transduced echo signal, such as conditioning, delaying, filtering, or otherwise processing the received echo 104B. Signal processing can further include converting the received energy from an analog signal representation into a digital representation, such as using one or more of the analog-to-digital converters. Such a digital representation can include real-valued information representative of the received energy, or a complex-valued representation that can include real or imaginary parts. The region of interest 132 can also or alternatively be disrupted using focused ultrasound by first processor circuit 122 instructing one or more transducers 111 to transmit a low-intensity ultrasound signal. Such disruption can disrupt the BBB, for example, to enable a neurotoxin to enter the target region of interest 132.

One or more techniques such as included in the examples below can be machine-implemented or computer implemented, such as performed by the system 100 corresponding to transitory or non-transitory instructions stored in one or more of the memory circuit 124, or stored or obtained from one or more other locations. In an example, one or more of the memory circuit 124 can include a processor-readable medium, such as comprising transitory or non-transitory instructions that, when performed by the first or second processors 122, 118, cause the processors or system 100 to perform one or more of the techniques included in the examples discussed below and in relation to other FIGS. such as FIG. 4, as illustrative examples.

In an example, the transducer array 111 can be configured to insonify the region of interest 132 using ultrasonic or acoustic energy, and the region of interest 132 can include a tissue region (e.g., a blood vessel region, or one or more other locations). In such an illustrative example, the target 186 can represent a tissue region of interest 132. Transducer array 111 can be configured to insonify the region of interest 132 using low intensity ultrasonic energy to a barrier 187 of parenchymal tissue. For example, the parenchymal tissue may include a target region of a brain and transducer array 111 may be configured to disrupt the BBB in the region of interest 132. Dashed lines in target 186 show disrupted section of barrier 187 and solid lines of barrier 187 indicate presence of undisrupted sections of barrier 187. Particularly, while target 186 is being insonified by transducer array 111, barrier 187 is disrupted in the area being insonified. This allows a therapeutic agent to enter target 186 where barrier 187 is disrupted and not enter regions outside of target 186 where barrier 187 is not disrupted. In this manner, an effect of the therapeutic agent is localized to a specified region while sparing or otherwise avoiding treatment of tissue in the surrounding region. In some examples, target 186 may correspond to a brain of a subject and barrier 187 may represent the BBB in the brain. In such circumstances, microbubbles may be introduced in the region of interest 132 to assist in reducing the energy needed by transducer array 111 to disrupt the BBB in the region of interest 132 to enable a neurotoxin to enter the region of interest 132.

The phrase "microbubbles" can generally refer to lipid-shelled perfluorocarbon gas bubbles that may be used as ultrasound contrast agents for medical imaging due to their high echogenicity and biocompatibility. Microbubbles generally exhibit a nonlinear response when insonified at diagnostic ultrasound frequencies. Such a response can be distinguishable from linear acoustic reflections. Linear reflections 104B or echoes generally refer to fundamental, nonharmonic echoes 104B produced by most tissues. The behavior exhibited by microbubbles when insonified cause the BBB to be disrupted in the target region being insonified.

As an illustrative example, biotinylated gas-filled microbubbles may be produced by an insonification protocol from decafluorobutane gas by dispersing gas in a lipid micellar mixture of distearoyl phosphatidylcholine, polyethylene glycol stearate, and biotin-PEG3400-distearoylphosphatidylethanolamine in normal saline to create microbubbles coated with a lipid monolayer shell. After preparation, microbubbles can be sealed in vials under decafluorobutane headspace atmosphere and stored refrigerated.

Biotinylated microbubbles can be conjugated to biotinylated antimouse VEGFR2 antibody using streptavidin as a linking molecule. Streptavidin may be added to the biotinylated microbubble solution at a concentration of 3 micrograms (µg) per 10 million microbubbles and incubated for 15 minutes at room temperature. During incubation, the microbubbles can be gently agitated every 2 minutes to ensure mixing. The microbubble solution may be washed twice with phosphate-buffered saline to remove excess streptavidin and counted again. The biotinylated anti-VEGFR2 antibody may be added to the microbubbles at 1.5 µg per 10 million microbubbles and incubated for 10 minutes. Two more washing operations may be performed to remove the excess antibody. Microbubble count and size distribution may be acquired before each experiment.

In some embodiments, computer system 126 (first and/or second processor circuit 122) may instruct magnetic resonance system 150 to capture one or more magnetic resonance images of a subject in region of interest 132. For example, computer system 126 may instruct magnetic resonance system 150 to capture images of region of interest 132 in accordance with T1-weighted spin echo imaging, T2-weighted gradient recalled echo imaging, and/or T2-weighted turbo spin-echo imaging. The images may be stored in memory circuit 124. Computer system 126 may retrieve, from memory circuit 124, a model representing one or more neurological diseases. Computer system 126 may compare various sections of region of interest 132 in the captured images to the model to determine a level of similarity between images of the various sections and the model. Computer system 126 may retrieve a threshold from memory circuit 124 and compare the retrieved threshold to the level of similarity that is determined. In response to determining that the level of similarity between images of a first section of region of interest 132 and the model exceed a threshold, computer system 126 may select a first section of region of interest 132 as target 186. Particularly, computer system 126 may determine that, because the level of similarly exceeds a threshold, the first section of region of interest 132 may have a strong likelihood of having a neurological disease.

In some implementations, in response to determining that the level of similarity between images of a first section of region of interest 132 and the model exceed a threshold, computer system 126 may retrieve one or more therapeutic solutions to address the neurological disease in the first section. For example, computer system 126 may determine that the neurological disease in a first section corresponds to epilepsy or a movement disorder. In such circumstances, computer system 126 may determine that a therapeutic solution to the determined neurological disease includes disconnecting critical pathways in the first section of region of interest 132. Accordingly, computer system 126 may select to administer a therapeutic agent that includes a neurotoxin to the first section of region of interest 132. For example, computer system 126 may determine that the neurotoxin that includes quinolinic acid may be used to disconnect critical pathways in the parenchymal tissue. Quinolinic acid is a major tryptophan metabolite produced by the kynurenine pathway. Quinolinic acid possess agonist properties at the N-methyl-Daspartate (NMDA)-type of glutamate receptor and, at appropriate concentrations, produces excitotoxic neuronal death in the brain. Under neuroinflammatory conditions, QA is produced by activated microglia and infiltrating macrophages, which can contribute to neurotoxicity. A variety of deleterious events that are related to NMDA receptor activation may be implicated by QA toxicity including increased intracellular Ca2+ concentrations, mitochondrial dysfunction, cytochrome C release, decreased ATP production, formation of damaging free radicals, oxidative stress, lipid peroxidation, neuroinflammation, and others. QA can also increase glutamate release and decrease glutamate uptake which potentially aggravates an already excitotoxic environment. In some embodiments, the therapeutic agent may include microbubbles and the neurotoxin. In some circumstances, target 186 may include a barrier 187 that prevents entrance of the therapeutic agent in the parenchymal tissue.

In some implementations, computer system 126 may determine a quantity of the neurotoxin needed to address the determined neurological disease. Computer system 126 may generate an instruction to administer the therapeutic agent. For example, computer system 126 may transmit an instruction to display 110 that indicates the type and amount of therapeutic agent to administer to a subject. For example, computer system 126 may indicate the administration of 0.06 nmoles of QA. A technician or doctor may read the instruction from display 110 and inject the subject with the appropriate quantity and type of therapeutic agent. In some embodiments, the technician or doctor may provide an instruction using audio or tactile input 121, 116 confirming the specified type and amount of therapeutic agent indicated by display 110. In response to receiving the confirmation, computer system 126 may instruct an injection system (or administration system) to automatically inject the therapeutic agent to the subject with the type and quantity specified. The injection system may be connected intravenously, or orally to a subject. The injection system may include a variety of combinations of chemicals or therapeutics or may include a single dose of the therapeutic agent (e.g., QA and microbubbles combination). The injection system may receive instructions from a technician or computer system 126 and in response may select and administer the appropriate type and amount of therapeutic agent to a subject.

In some embodiments, computer system 126 may present on display 110 MR images of region 132 stored in memory 123. A technician or doctor may select target 186 by providing tactile or audio input 116, 121 identifying target 186. For example, the technician or doctor may determine which portion of parenchymal tissue in images of region 132 correspond to a neurological disease. The technician or doctor, after identifying the neurological disease in target 186, may select the therapeutic agent for administration to target 186. The technician or doctor may then instruct computer system 126 to insonify target 186 to disrupt barrier 187 in target 186 to allow the therapeutic agent to permeate parenchymal tissue in target 186.

In some embodiments, the therapeutic agent may include microbubbles and the neurotoxin. In some circumstances, target 186 may include a barrier 187 that prevents entrance of the therapeutic agent in the parenchymal tissue. In such circumstances, computer system 126 may instruct transducer array 111 to insonify target 186 using, for example, low intensity ultrasound or any other acoustic energy. In response to target 186 being insonified, barrier 187 is disrupted allowing the therapeutic agent to enter parenchymal tissue in target 186. In an example, target 186 may be a brain section (e.g., hippocampus) and barrier 187 may be the BBB. In such circumstances, insonifying target 186 may transienty disrupt the BBB allowing the therapeutic agent (e.g., QA) to permeate the section of the brain being insonified.

After insonifying target 126, computer system 126 may instruct MR system 150 to capture additional images of region of interest 132. For example, computer system 126 may instruct MR system 150 to generate and store additional images after a predetermined period of time (e.g., after 1 day, then again after 7 days). These images may be generated in accordance with T1-weighted spin echo imaging, T2-weighted gradient recalled echo imaging, and/or T2-weighted turbo spin-echo imaging. The imaging technique used to capture images after insonification of target 186 and administration of the therapeutic agent may be the same or different as the imaging used to detect, identify and select target 186 prior to insonification.

In an example, target 186 may be the CA3 region of the hippocampus of a subject. After the therapeutic agent that includes QA and microbubbles is intravenously-administered to the subject, target 186 is insonified using a low intensity focused ultrasound. A contrast agent, such as, gadodiamide contrast may also be administered to the subject. After insonifying target 186, T1-weighted spin echo imaging (T1) may be captured using magnetic resonance system 150. The images may be stored in memory circuit 124 and presented on display 110. Computer system 126 and/or a technician may process the images to determine whether extravasation of the gadodiamide contrast is present at a location in the images corresponding to target 186. In response to determining that extravasation of the gadodiamide contrast at a location in the images corresponding to target 186, computer system 126 and/or the technician may confirm that barrier 187 (e.g., the BBB in the brain) was opened successfully. T2-weighted gradient recalled echo (T2*-GRE) imaging may be used to detect the presence of small lesions in target 186. Accordingly, computer system 126 may instruct magnetic resonance system 150 to capture additional images using T2*-GRE of target 186 after target 186 is insonified. These additional images may then be presented on display 110 or processed to determine whether lesions are present in target 186. For example, computer system 126 may instruct magnetic resonance system 150 to capture additional images using T2*-GRE of target 186 after 1 day and after 7 days of insonifying target 186. Any other period of time may be used for this process. Computer system 126 may retrieve an image of target 186 captured before being insonified and exposed to the therapeutic agent and one of the images captured after a predetermined period of time. Computer system 126 may compare the two images to detect a difference in the images and determine whether the difference represents a lesion in target 186. Particularly, computer system 126 may determine whether target 186 includes an increase in the number of small cell bodies surrounding the area of neuronal loss in the field of insonification. In response to such determination, computer system 126 may conclude and inform a technician that parenchymal tissue in target 186 has been destroyed.

For example, computer system 126 retrieve an image 210 (FIG. 2) representing target 186 seven days after being insonified after being exposed to the therapeutic agent (QA and microbubbles). Computer system 126 may determine that region 220 differs from an image 210 of target 186 pre-insonification and represents neuronal loss. Particularly, computer system 126 may analyze magnified versions 230 of region 220 to determine that sections 232 represent borders of the layer where neuronal loss occurred and detect the presence in section 234 of ionized calcium binding adapter molecule 1 (IBA-1) immunolabeling.

An illustrative example is described below, concerning a study of techniques herein as applied to a particular subject. Male Sprague Dawley rats (e.g., 5-6 weeks of age (120-150 g)), were divided into two groups receiving the following treatments: 1) MRgFUS+microbubbles+saline (n=5), or 2) MRgFUS+microbubbles+QA (n=5). QA was dissolved in 0.1M PBS (10 mg/ml). Either 1 ml of the QA solution (0.06 mmol) or 1 ml of saline was injected intraperitoneally once per day for 4 days beginning 2 days prior to insonification. Phospholipid encapsulated microbubbles (mean size: ~5 um; concentration: $6\times10^8$ microbubbles/ml; volume injected: 300 µl/kg) and Gadodiamide contrast (Omniscan, 0.2 ml/kg) were delivered via the tail vein just prior to sonification.

An acoustic energy delivery system was configured in a manner similar to that discussed above as in system 100 and in this illustrative example, the system included an MR-compatible, pre-focused, 8-element annular array comprising 1.5 MHz transducers 111 (e.g., having spherical radius=20 mm±2 mm, active diameter=25 mm [focal ratio=0.8]; an ultrasonic transducer with 80% electric-acoustic efficiency, which was connected to a phased array generator and RF power amplifier. An MR-compatible motorized positioning stage was used to move the transducer in the rostral-caudal and medial-lateral directions. The focus was moved along the direction of ultrasound beam by electronic steering. The membrane in front of the transducer was filled with degassed water and inflated to ensure good ultrasonic coupling between the membrane and the head of the animal.

After placing the animal in the MR scanner, a gradient echo scout sequence was run to determine the position of the animal's head relative to the transducer (TR/TE=57/5 milliseconds, flip angle=25°, 1 average, FOV=45 mm, matrix size=128×128, slice thickness=1.5 mm) and to detect air bubbles at the membrane/skin interface. Initially, a single shot of insonification with low electric power (typically 25% of maximum power, i.e., 6.7 watt, during 5 s) was performed to locate the focal plane with a mild temperature elevation of 3 to 5° C. The focus was then adjusted to target the lateral aspect of the hippocampus. Treatments included up to five points of sonification. The insonification zones were moved slightly rostral-caudally and dorsal-ventrally in the vicinity of the identified target (1.5 MHz, 0.69 MPa, wave packet 20-msec, duty cycle of 2%, 1 Hz burst repetition frequency, 120-sec duration).

Post-contrast T1-weighted spin echo imaging (TR/TE=650/12 milliseconds, flip angle 1=90 degrees, flip angle 2=180 degrees, 2 averages, FOV=35 mm, matrix size=256×256, slice thickness 1.0 mm) and T2*-weighted gradient echo imaging (TR/TE=600/10 milliseconds, flip angle=25°, 2 averages, FOV=40 mm, matrix size=192×192, slice thickness 1.3 mm) were performed immediately after insonification to evaluate blood-brain barrier opening and possible injury, respectively. In order to assess for possible lesions during the follow-up period, T2-weighted TSE images (TR/TE=2000/74 milliseconds, turbo factor=7, 3 averages, FOV=40 mm, matrix size=256×256, slice thickness 1.0 mm), were acquired at 3 time points: immediately, 1 day, and 7 days after sonification.

24 hours post-insonification using T2-TSE imaging, the brains of saline-treated animals were normal in appearance. In contrast, images 210 of brains from QA-treated animals exhibited hyperintensity in the area of insonification. The images 210 revealed that the presumed lesion affected the hippocampus, particularly the lateral aspect of the CA3 subregion. A small area in the most dorso-lateral aspect of the thalamus, adjacent to the hippocampus, also appeared to be affected. 7 days post-insonification using T2-TSE imaging, images 210 from saline-treated animals appeared normal with no evidence of a lesion. In contrast, the QA-treated animals exhibited signs of damage in the region of insonification. Areas of increased signal intensity were observed in the target region, indicative of lesions to the brain parenchyma as targeted. The imaging protocols and focused ultrasound delivery protocols mentioned in the illustrative example discussed above describe one approach, and other imaging protocols and ultrasound delivery protocols may be used.

FIG. 3 illustrates an exemplary flowchart of a process 300 for using acoustic energy and a therapeutic agent in accordance with various embodiments. At step 310, imaging data corresponding to a region of interest 132 is obtained, the region of interest 132 within an imaging subject. For example, computer system 126 may instruct MR system 150 to generate and capture one or more images of region of interest 132. MR system 150 may store the captured images in memory circuit 124.

At step 320, information indicative of a target region within the region of interest 132 is received from the obtained imaging data. For example, computer system 126 may compare the region of interest 132 in one or more images stored in memory circuit 124 using a model of images that represent a disease. Computer system 126 may determine whether a similarity between a section of a plurality of sections in the one or more images and the images in the model exceeds a threshold. In response to determining, that the similarity exceeds the threshold, computer system 126 may select the section of the image as the target region. In some embodiments, instead of or in addition to computer system 126 searching for the target area of interest, a user input may be received using input 116 or 121 selecting the target area from an image of region of interest 132 presented on display 110. For example, a user input may circle, highlight or otherwise mark sections of the region of interest 132 to specify target 186.

At step 330, focused acoustic energy directed to the target region within the region of interest 132 is generated to disrupt a barrier 187 between a therapeutic agent and parenchymal tissue in response to insonification by the focused acoustic energy, the therapeutic agent comprising a neurotoxin and microbubbles. For example, computer system 126 and/or a technician or doctor may administer a therapeutic agent to a subject. The therapeutic agent may include a neurotoxin and/or microbubbles. The neurotoxin may include QA (e.g., when target 186 is a region of the brain). After administering the therapeutic agent, computer system 126 may instruct transducer array 111 to transmit focused acoustic energy (e.g., low intensity ultrasound) directed at target 186. As a result of transmitting the focused acoustic energy, barrier 187 (e.g., which prevents the neurotoxin from entering parenchymal tissue in target 186) is disrupted (e.g., removed or has its chemical properties altered temporarily) to enable the therapeutic agent including the neurotoxin to enter target 186. Barrier 187 outside of the focused acoustic energy (outside of the dotted circle) is not disrupted and continues to prevent the therapeutic agent including the neurotoxin from permeating the parenchymal tissue in region of interest 132.

Figure 4:
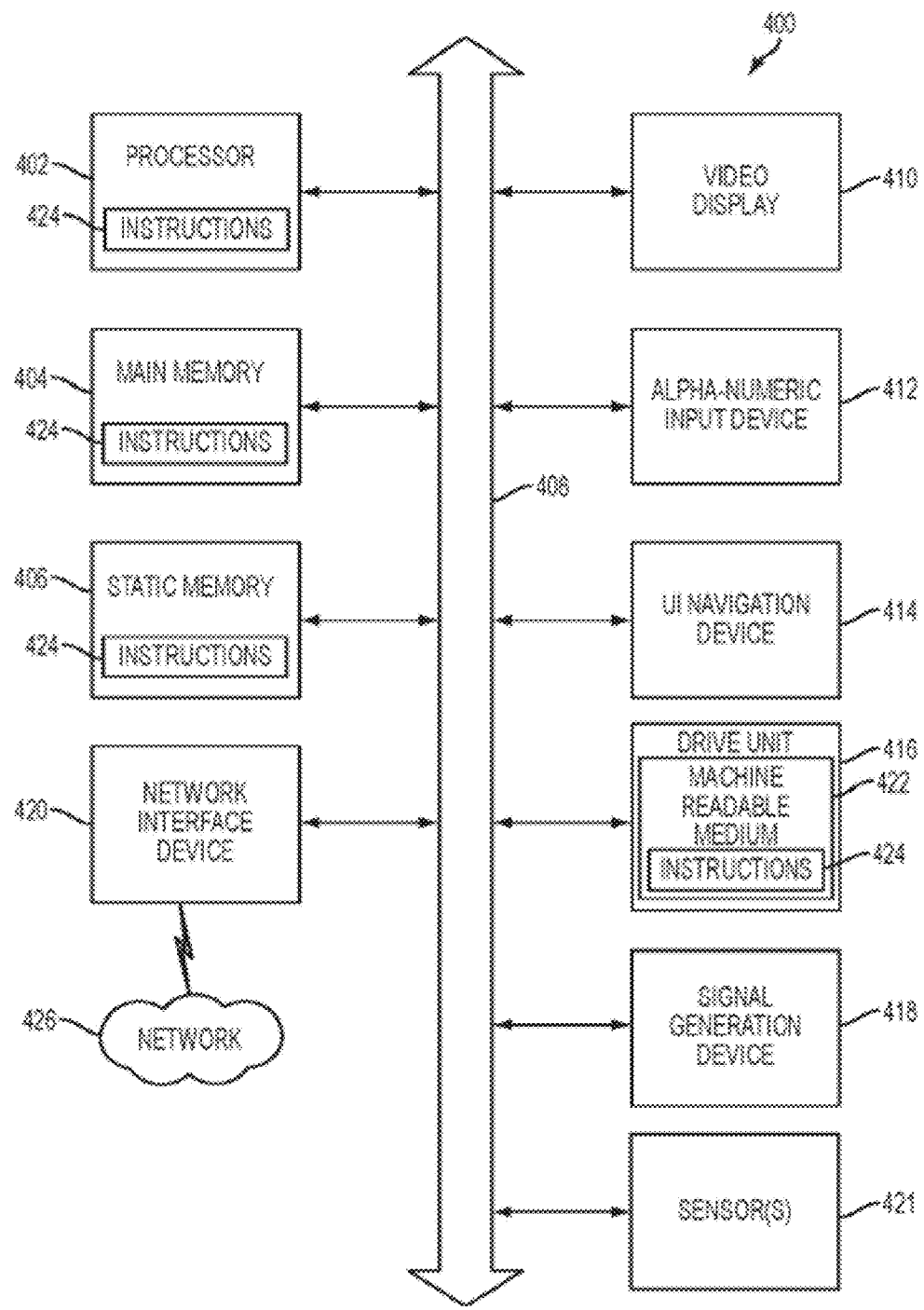
FIG. 4 illustrates generally a block diagram of an example that can include a machine upon which one or more embodiments (e.g., discussed methodologies described herein) can be implemented (e.g., run), such as where the machine is included as a portion of the system shown in FIG. 1 or where the system in FIG. 1 is communicatively coupled to the machine of FIG. 4.

FIG. 4 illustrates generally a block diagram of an example that can include a machine 400 upon which one or more embodiments (e.g., discussed methodologies described herein) can be implemented (e.g., run), such as where the machine is included as a portion of the system 100 shown in FIG. 1 or where the system 100 in FIG. 1 is communicatively coupled to the machine 400 of FIG. 4. Examples of the machine 400 can include logic, one or more components, or circuits. Circuits are tangible entities configured to perform certain operations. In an example, circuits can be arranged (e.g., internally or with respect to external entities such as other circuits) in a specified manner. In an example, one or more computer systems 126 (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field-programmable gate array (FPGA) or an application-specific integrated circuit (ASIC). In an example, a circuit can include programmable logic (e.g., circuitry, as encompassed within a general-purpose processor or other programmable processor) that can be temporarily configured (e.g., by software) to perform the certain operations. It will be appreciated that apparatus and techniques described herein can be implemented in a circuit mechanically (e.g., in dedicated and permanently configured circuitry), or in temporarily configured circuitry (e.g., configured by software).

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where a multiple of such circuits exist contemporaneously, communications can be achieved through signal transmission (e.g., over appropriate circuits and buses that connect the circuits. In embodiments in which multiple circuits are configured or instantiated at different times, communications between such circuits can be achieved, for example, through the storage and retrieval of information in memory structures to which at least one of the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of techniques described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Generally, the techniques described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment, or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Examples of various embodiments (e.g., apparatus, systems, or methods) can be implemented in digital electronic circuitry, in computer hardware, in firmware, in software, or in any combination thereof. Examples of various embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Certain functionality can be implemented in permanently configured hardware (e.g., an ASIC), or in temporarily configured hardware (e.g., a combination of software and a programmable processor), for example.

In an example, the machine 400 can operate as a stand-alone device or the machine 400 can be connected (e.g., networked) to other machines. In a networked deployment, the machine 400 can operate in the capacity of either a server or a client machine in server-client network environments. In an example, the machine 400 can act as a peer machine in peer-to-peer (or other distributed) network environments. The machine 400 can be a personal computer (PC), a tablet PC, a set-top box (STB), a Personal Digital Assistant (PDA), a hand-held application-specific assembly, a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

In an example, the machine (e.g., computer system 126) 400 can include a processor 402 (e.g., a central processing unit (CPU), a graphics processing unit (GPU) or both), a main memory 404 and a static memory 406, some or all of which can communicate with each other via a bus 408 or other link. The machine 400 can further include a display unit 410, an alphanumeric input device 412 (e.g., a keyboard), and a user interface (UI) navigation device 411 (e.g., a mouse, a touch-screen, or one or more soft-keys, as illustrative examples). In an example, the display unit 410, input device 412 and UI navigation device 411 can be a touch screen display. The machine 400 can additionally include a storage device (e.g., drive unit) 416, a signal generation device 418 (e.g., a speaker), a network interface device 420, and one or more sensors 421, such as a global positioning system (GPS) sensor, compass, accelerometer, or other sensor.

The storage device 416 can include a machine readable medium 422 on which is stored one or more sets of data structures or instructions 424 (e.g., software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the main memory 404, the static memory 406, or the storage device 416 can comprise a machine readable medium or machine readable media 422.

While the machine readable medium 422 is illustrated as a single medium, the term "machine readable medium" can include a single medium or multiple media (e.g., a centralized or distributed database, and/or associated caches and servers) that can be configured to store the one or more instructions 424. The term "machine readable medium" can also be taken to include any tangible medium that is capable of storing, encoding, or carrying instructions 424 for execution by the machine 400 and that cause the machine 400 to perform any one or more of the methodologies of the present disclosure or that is capable of storing, encoding or carrying data structures utilized by or associated with such instructions 424. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone Service (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions 424 for execution by the machine 400, and includes digital or analog communications signals or other intangible medium to facilitate communication of such software.

Various Notes

Each of the non-limiting aspects described herein can stand on its own, or can be combined in various permutations or combinations with one or more of the other aspects or other subject matter described in this document.

The above detailed description includes references to the accompanying drawings, which form a part of the detailed description. The drawings show, by way of illustration, specific embodiments in which the invention can be practiced. These embodiments are also referred to generally as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method, comprising:
   obtaining imaging data corresponding to a region of interest, the region of interest within an imaging subject;
   receiving information indicative of a target region within the region of interest from the obtained imaging data, the target region comprising pathways contributing to neurological disease; and
   while a therapeutic agent is being delivered to the imaging subject, generating focused acoustic energy directed to the target region within the region of interest to disrupt a barrier between a therapeutic agent and parenchymal tissue in response to insonification by the focused acoustic energy, the therapeutic agent comprising a neurotoxin and microbubbles, wherein the neurotoxin comprises quinolinic acid and the microbubbles comprise lipid-shelled perfluorocarbon gas bubbles;
      causing the therapeutic agent comprising the neurotoxin and microbubbles to enter the target region within the region of interest comprising a brain of the imaging subject while the target region is being insonified by the focused acoustic energy; and
      causing disconnection of the pathways contributing to the neurological disease by the therapeutic agent that entered the target region in response to interaction between the focused acoustic energy directed to the target region and presence of the therapeutic agent within the target region.

2. The method of claim 1, wherein the focused acoustic energy comprises ultrasound generated by an acoustic transducer, and wherein receiving the information indicative of the target region within the region of interest comprises performing an image segmentation technique.

3. The method of claim 1, wherein obtaining the imaging data comprises generating a magnetic resonance imaging sequence and constructing an image of the region of interest in response to excitation associated with the magnetic resonance imaging sequence.

4. The method of claim 3, wherein the imaging sequence corresponds to at least one of a T1-weighted spin echo imaging protocol, a T2-weighted gradient recalled echo imaging protocol, or a T2-weighted turbo spin-echo imaging protocol.

5. The method of claim 3 further comprising enhancing contrast shown in a constructed image using a contrast agent administered in relation to the magnetic resonance imaging sequence.

6. The method of claim 1 further comprising administering the therapeutic agent.

7. The method of claim 1, wherein:
   the region of interest comprises a brain of the imaging subject;
   the barrier comprises blood-brain-barrier (BBB); and
   the neurotoxin comprises a chemical with substantially low BBB permeability.

8. The method of claim 1, wherein receiving information indicative of the target region within the region of interest comprises:
   comparing the imaging data of a plurality of sections within the region of interest to a model representing neurological disease;
   determining that a level of similarity between a first of the plurality of sections and the model exceeds a threshold; and
   in response to determining that the level of similarity exceeds the threshold, selecting as the target region the first of the plurality of sections.

9. The method of claim 1, wherein receiving information indicative of the target region within the region of interest comprises receiving user input that selects the target region from a plurality of regions in the region of interest.

10. A system, comprising:
    a magnetic resonance imaging system configured to obtain imaging data corresponding to a region of interest, the region of interest within an imaging subject;
    a memory circuit configured to store the obtained imaging data;
    a processor circuit coupled to a memory circuit and configured to receive information indicative of a target region within the region of interest from the stored imaging data, the target region comprising pathways contributing to neurological disease;
    an acoustic energy generator coupled to an acoustic transducer configured to, while a therapeutic agent is being delivered to the imaging subject, generate focused acoustic energy directed to the target region within the region of interest to disrupt a barrier between a therapeutic agent and parenchymal tissue in response to insonification by the focused acoustic energy, the therapeutic agent comprising a neurotoxin and microbubbles, wherein the neurotoxin comprises quinolinic acid and the microbubbles comprise lipid-shelled perfluorocarbon gas bubbles, the acoustic energy generator causing the therapeutic agent comprising the neurotoxin and microbubbles to enter the target region within the region of interest comprising a brain of the imaging subject while the target region is being insonified by the focused acoustic energy, and wherein the acoustic energy generator causes disconnection of the pathways contributing to the neurological disease by the therapeutic agent that entered the target region in response to interaction between the focused acoustic energy directed to the target region and presence of the therapeutic agent within the target region.

11. The method of claim 1, further comprising:
    capturing a T1-weighted spin echo image using a magnetic resonance system after the therapeutic agent is administered to the imaging subject;
    detecting presence of a contrast agent at the target region indicating that the barrier has been opened based on the T1-weighted spin echo image;
    after capturing the T1-weighted spin echo image and after the target region is insonified by the focused acoustic energy, capturing one or more T2-weighted gradient recalled echo images to detect presence of lesions in the target region.

12. The method of claim 11, further comprising determining that the parenchymal tissue in the target region has been destroyed in response to determining that the target region includes an increased number of small cell bodies using the one or more T2-weighted gradient recalled echo images.

13. The method of claim 12, further comprising detecting presence of an ionized calcium binding adapter molecule 1 in the target region to determine that the parenchymal tissue in the target region has been destroyed.

14. The method of claim 1, wherein the microbubbles exhibit a nonlinear response when insonified at diagnostic ultrasound frequencies that is distinguishable from linear acoustic reflections.

15. The system of claim 10, wherein the processor circuit is configured to receive information indicative of the target region within the region of interest by:
comparing the imaging data of a plurality of sections within the region of interest to a model representing neurological disease;
determining that a level of similarity between a first of the plurality of sections and the model exceeds a threshold; and
in response to determining that the level of similarity exceeds the threshold, selecting as the target region the first of the plurality of sections.

16. The system of claim 10, wherein the processor circuit is configured to receive information indicative of the target region within the region of interest by receiving user input that selects the target region from a plurality of regions in the region of interest.

17. An apparatus, comprising:
means for obtaining imaging data corresponding to a region of interest, the region of interest within an imaging subject;
means for receiving information indicative of a target region within the region of interest from the obtained imaging data, the target region comprising pathways contributing to neurological disease; and
means for while a therapeutic agent is being delivered to the imaging subject, generating focused acoustic energy directed to the target region within the region of interest to disrupt a barrier between a therapeutic agent and parenchymal tissue in response to insonification by the focused acoustic energy, the therapeutic agent comprising a neurotoxin and microbubbles, wherein the neurotoxin comprises quinolinic acid and the microbubbles comprise lipid-shelled perfluorocarbon gas bubbles;
means for causing the therapeutic agent comprising the neurotoxin and microbubbles to enter the target region within the region of interest comprising a brain of the imaging subject while the target region is being insonified by the focused acoustic energy; and
means for causing disconnection of the pathways contributing to the neurological disease by the therapeutic agent that entered the target region in response to interaction between the focused acoustic energy directed to the target region and presence of the therapeutic agent within the target region.

18. The apparatus of claim 17, wherein means for obtaining the imaging data comprises means for generating a magnetic resonance imaging sequence and means for constructing an image of the region of interest in response to excitation associated with the magnetic resonance imaging sequence.

19. The apparatus of claim 18, wherein the imaging sequence corresponds to at least one of a T1-weighted spin echo imaging protocol, a T2-weighted gradient recalled echo imaging protocol, or a T2-weighted turbo spin-echo imaging protocol.

20. The apparatus of claim 17, wherein:
the region of interest comprises a brain of the imaging subject;
the barrier comprises blood-brain-barrier (BBB); and
the neurotoxin comprises a chemical with substantially low BBB permeability.

21. The apparatus of claim 17, wherein means for receiving information indicative of the target region within the region of interest comprises:
means for comparing the imaging data of a plurality of sections within the region of interest to a model representing neurological disease;
means for determining that a level of similarity between a first of the plurality of sections and the model exceeds a threshold; and
means for in response to determining that the level of similarity exceeds the threshold, selecting as the target region the first of the plurality of sections.

* * * * *